United States Patent [19]

Rasheed

[11] Patent Number: 5,919,975
[45] Date of Patent: Jul. 6, 1999

[54] AROMATIC AND ALIPHATIC SULFONATES AND PROPERTIES AND APPLICATIONS THEREOF

[75] Inventor: Khalid Rasheed, Missouri City, Tex.

[73] Assignee: Witco Corporation, Greenwich, Conn.

[21] Appl. No.: 08/655,992

[22] Filed: May 31, 1996

[51] Int. Cl.$^6$ .................................................. C07C 309/10
[52] U.S. Cl. ........................................ 562/110; 562/103
[58] Field of Search .................................... 562/101, 103, 562/110

[56] References Cited

U.S. PATENT DOCUMENTS

| | | |
|---|---|---|
| 3,082,249 | 3/1963 | Gaertner . |
| 3,243,455 | 3/1966 | Pizzini et al. . |
| 3,377,234 | 4/1968 | Illingworth . |
| 3,932,206 | 1/1976 | Illingworth et al. . |
| 3,986,922 | 10/1976 | Parker et al. . |
| 4,180,470 | 12/1979 | Tokosh et al. . |
| 4,311,552 | 1/1982 | Brucato et al. . |
| 4,518,459 | 5/1985 | Freis et al. . |
| 4,594,200 | 6/1986 | Penny . |
| 4,618,400 | 10/1986 | Wood et al. . |
| 4,666,558 | 5/1987 | Wood et al. . |
| 4,786,364 | 11/1988 | Tefft . |
| 4,820,379 | 4/1989 | Darlington . |
| 4,935,096 | 6/1990 | Gallagher et al. . |
| 4,964,949 | 10/1990 | Hamaguchi et al. . |
| 4,976,743 | 12/1990 | Ohba et al. . |
| 5,049,311 | 9/1991 | Rasheed et al. . |
| 5,094,716 | 3/1992 | Letscher . |
| 5,100,574 | 3/1992 | Urushibata et al. . |
| 5,102,500 | 4/1992 | Darlington . |
| 5,120,397 | 6/1992 | Urushibata et al. . |
| 5,141,598 | 8/1992 | Richman et al. . |
| 5,151,155 | 9/1992 | Cody et al. . |
| 5,158,697 | 10/1992 | Kawamori et al. . |
| 5,259,969 | 11/1993 | Srivatsa et al. . |
| 5,281,348 | 1/1994 | Letscher . |
| 5,282,928 | 2/1994 | Takahashi et al. . |
| 5,282,997 | 2/1994 | Richmann et al. . |
| 5,302,377 | 4/1994 | Pereira et al. . |
| 5,304,316 | 4/1994 | Urushibata . |
| 5,414,144 | 5/1995 | Watanabe et al. . |
| 5,417,807 | 5/1995 | Fossas et al. . |
| 5,417,808 | 5/1995 | Okamoto et al. . |
| 5,425,891 | 6/1995 | Pujo et al. . |

FOREIGN PATENT DOCUMENTS

| | | |
|---|---|---|
| 0 434 084 | 6/1991 | European Pat. Off. . |
| 62-121775 | 6/1987 | Japan . |
| 5-311200 | 11/1993 | Japan . |
| 7-26416 | 1/1995 | Japan . |
| 8-199187 | 8/1996 | Japan . |

OTHER PUBLICATIONS

Mak, et al., "Characteristics of Fatty Acid As an Effective Flotation Deinking Collector," *2d Research Forum on Recycling*, 145–152 (1993).

Hans–Joachim Putz, et al., "Deinking of Oil–and Water–born Printing Inks—A new flotation Deinking Model," *Recycling Forum*, 183–190 (1991).

Borchardt, "Chemical Structure–Property Relationships of Deinking Surfactants," *Progress in Paper Recycling*, 1(2):45–60 (Feb. 1992).

Borchardt, An Introduction To Deinking Surfactants, *Recycling Symposium*, 131–139 (1993).

*Primary Examiner*—Robert Gerstl
*Attorney, Agent, or Firm*—Edward K. Welch; Timothy X. Witkowski; Andrew S. Reiskind

[57] ABSTRACT

The present invention is directed to novel alkyl glyceryl ether disulfonate compositions (ADEDS), alkylphenol polyethoxy sulfate-sulfonates, and ethoxylated alkylphenol sulfonates, and novel methods of preparation and uses thereof.

7 Claims, No Drawings

AROMATIC AND ALIPHATIC SULFONATES AND PROPERTIES AND APPLICATIONS THEREOF

BACKGROUND OF THE INVENTION

Both aromatic and aliphatic sulfates and sulfonates are an important group of anionic surface-active agents used extensively in a number of industrial applications. These include operations in drilling for and recovery of crude oil; emulsifiers for pesticides used in crop protection; in shampoos and creams for personal care; laundry detergents; hard surface cleaners; emulsifiers for emulsion polymerization systems; lubricants; wetting agents; and dispersants in a variety of specialized industrial applications. Sulfates, being susceptible to breakdown in acidic environments, are limited to formulations used in weakly acidic or basic systems. Although sulfonates can be used under both acidic and basic conditions, they cannot be efficiently used in high electrolyte systems. In hard waters, for example, they tend to precipitate out as insoluble calcium and magnesium salts.

The present invention relates to the synthesis and properties of novel sulfonates that are not only electrolyte tolerant and thermally stable, and can be used in the applications mentioned above, but also have other interesting and commercially useful properties.

SUMMARY OF THE INVENTION

The present invention is directed to novel alkyl diglyceryl ether disulfonate compositions (ADEDS), alkylphenol polyethoxy sulfate-sulfonates, and ethoxylated alkylphenol sulfonates, and their methods of preparation and uses.

One aspect of the present invention resides in a method for preparing an alkyl glyceryl ether disulfonate composition (ADEDS) which comprises a mixture of compounds of formula (I):

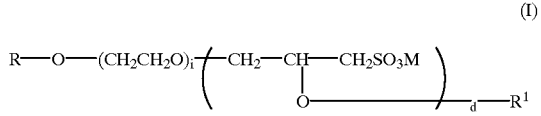

wherein i is an integer from 0 to 10;

M is a cation selected from the group consisting of lithium, sodium, potassium, ammonium, and mixtures thereof;

$R^1$ is (ALK—O)$_p$H or H, wherein p is an integer from 1 to 10 and each ALK is independently ethyl or propyl; and R is straight or branched alkyl or alkenyl containing 8 to 18 carbon atoms and 0 to 3 carbon-carbon double bonds, the mixture containing compounds of formula (I) wherein d is 1, 2, 3 and 4 and optionally 5, wherein the mole average value of d in the composition is 1.8 to 2.2, the method comprising:

a) forming a mixture of alkyl glyceryl halides of formula (II)

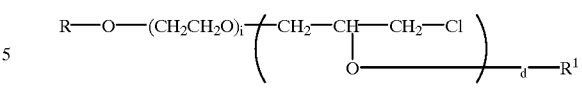

by reacting epichlorohydrin with an alcohol or alcohol ethoxylate of the formula R—O—(CH$_2$CH$_2$O)$_i$—H to form said mixture of compounds of formula (II) and then optionally alkoxylating the pendant hydroxyl group on said compounds of formula (II); and then b) replacing the chloro substituents on the compounds of formula (II) with —SO$_3$M.

Another aspect of the present invention is directed to a method of preparing an alkylphenol polyethoxy sulfate-sulfonate of formula (III):

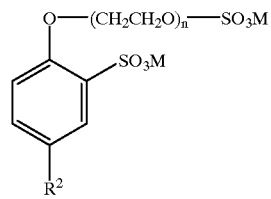

wherein $R^2$ is a straight or branched alkyl group containing 8–12 carbon atoms, M is lithium, sodium, potassium, or ammonium, and n is 6–10 comprising:

a) reacting an ethoxylated alkyl phenol of the formula $R^2$—Ph—O(CH$_2$CH$_2$O)$_n$H wherein $R^2$ and n are as defined above and Ph denotes a phenyl ring and the substituents thereon are in the para-position, with sulfur trioxide to form an intermediate of formula (IV):

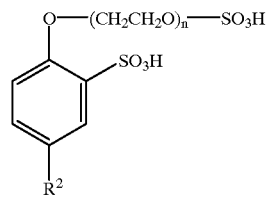

and b) reacting the sulfonated product (IV) of step (a) with a hydroxide of the formula M—OH under conditions wherein said product of formula (III) is formed.

A further aspect of the present invention is directed towards a method of preparing an ethoxylated alkylphenol sodium sulfonate of formula (V):

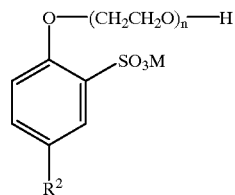

wherein $R^2$ is straight or branched alkyl containing 8 to 12 carbon atoms, M is lithium, sodium, potassium, or ammonium and n is 6 to 10, comprising:

a) reacting an ethoxylated alkylphenol of the formula $R^2$—Ph—O(CH$_2$CH$_2$O)$_n$H wherein $R^2$ and n are as defined above and Ph denotes a phenyl ring and the substituents thereon are in the para-position, with sulfur trioxide to form a product of formula (IV):

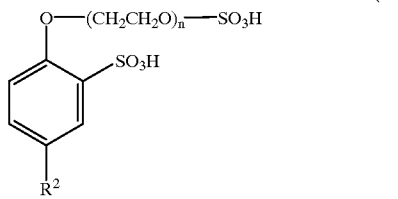

(IV)

and then b) reacting the sulfonated product of step (a) with a hydroxide of the formula M—OH under conditions wherein said product of formula (V) is formed.

The present invention further contemplates alkyl diglyceryl ether disulfonate compositions (ADEDS) comprising compounds of formula (I). The invention also contemplates alkylphenol polyethoxy sulfate-sulfonates of formula (III); and ethoxylated alkyl phenol sodium sulfonates of formula (V).

The present invention is further directed towards the use of compounds of the present invention in the manufacture of paper, particularly in that they optimize the effectiveness of wet strength resin additives for paper, and they increase the wet strength/dry tensile strength ratio which is very significant in the manufacture of paper products that may be creped or uncreped and paper that is through-dried or not, such as paper towels, paper napkins and similar paper products.

The present invention is also directed towards the use of compounds of the present invention in the beneficiation of ores by froth flotation.

The present invention is also directed towards the use of compounds of the present invention as emulsifiers in emulsion polymerization reactions.

The present invention is also directed towards the use of compounds of the present invention in hard surface cleaners, laundry spot removers, and detergents; in dyeing of fibers, e.g. nylon; and as brightening agents in metal electroplating baths.

The present invention is also directed towards the use of compounds of the present invention in the deinking of waste paper.

DETAILED DESCRIPTION OF THE PRESENT INVENTION

Compounds and Synthesis

The present invention is directed in one aspect towards novel alkyl diglyceryl ether disulfonates (ADEDS), alkylphenol polyethoxy sulfate-sulfonates, and ethoxylated alkylphenol sulfonates, and to novel methods of preparation of these compounds.

One aspect of the present invention resides in a process for preparing an alkyl diglyceryl ether disulfonate composition (ADEDS) which comprises a mixture of compounds of formula (I):

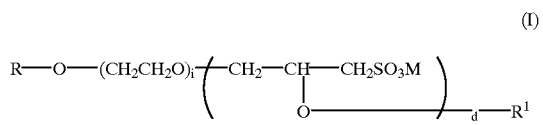

wherein i is an integer from 0 to 10;

M is selected from the group consisting of lithium, sodium, potassium, ammonium, and mixtures thereof;

$R^1$ is (ALK—O)pH or H, wherein p is an integer from 1 to 10, and R is straight or branched alkyl or alkenyl containing 8 to 18 carbon atoms and 0 to 3 carbon to carbon double bonds. The composition is a mixture of compounds wherein d is 1, 2, 3 and 4. Typically, compounds wherein d is 5 are also present, in trace amounts. Each ALK present can be ethyl or propyl; the preferred propyl group is isopropyl. Preferably, when $R^1$ is an alkoxylate group it is entirely ethoxylate or entirely propoxylate.

The preparation of the compound of formula (I) comprises reacting epichlorohydrin with an alcohol or alcohol ethoxylate of the formula R—O—(CH$_2$CH$_2$O)$_i$—H, wherein i and R are as defined above, under conditions wherein an intermediate compound of formula (II) is formed:

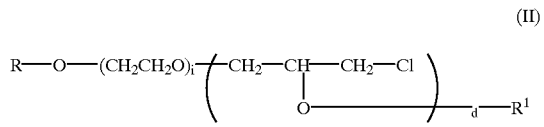

It should be understood that the reaction with epichlorohydrin generally forms a mixture of adducts formed as epichlorohydrin reacts with the pendant hydroxyl group left by addition of a previous molecule of epichlorohydrin. Typically, the reaction mass formed in production of the mixture of compounds of formula (II), carrying out the reaction under the conditions disclosed herein, is a mixture containing on the order of about 35 to 45% monoadduct, about 35 to 45% of diadduct, about 10 to 20% of triadduct, about 2 to 10% of tetraadduct, and optionally traces of pentaadduct. According to gas chromatographic analysis of a typical such reaction mass, the mass is a mixture of about 40% mono-adduct, about 40% of diadduct, about 15% of triadduct, about 5% of tetraadduct, and traces of pentaadduct.

The reaction with the epichlorohydrin to form the mixture of compounds of formula (II) is believed to form byproducts having either or both of the structures (II-A) and (II-B):

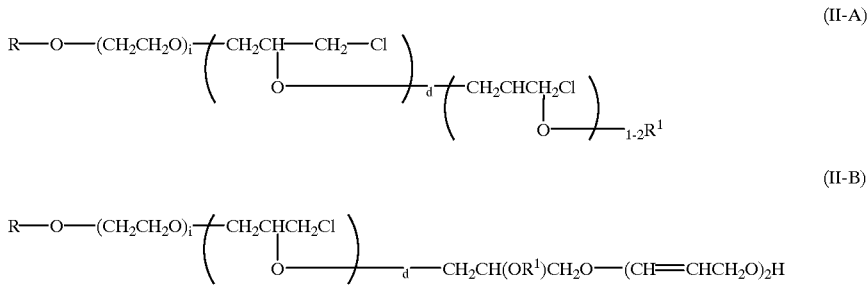

(II-A)

(II-B)

Employing the reaction conditions described herein generally leads to a reaction mixture wherein the mixture of compounds of formula (II) constitutes on the order of about 60% of the reaction mixture.

Preferably the reaction to form the product mixture of compounds of formula (II) involves an acid catalyzed addition of epichlorohydrin to the alcohol or alcohol ethoxylate in a 2:1 molar ratio of epichlorohydrin to alcohol or alcohol ethoxylate. The catalyst may be any protonic acid or Lewis acid suitable for acid catalyzed addition, preferably boron trifluoride.

At this point the pendant hydroxyl group of the intermediate compounds (II) wherein $R^1$ is -H may optionally be alkoxylated with 1 to 10 ethoxy and/or propoxy units. Preferred alkoxylates contain 2 to 6 ethoxy units or 2 to 4 propoxy units. The reaction is a conventional acid-catalyzed alkoxylation with ethylene oxide and/or propylene oxide. Boron trifluoride is the preferred catalyst.

The resulting mixture of compounds of formula (II) contains chloro substituents which are then replaced with $-SO_3M$. This reaction is performed under conditions sufficient to replace all the chloro substituents in (II) with $-SO_3M$. Preferably this reaction involves the reaction of the compounds of formula (II) and an aqueous solution of $M_2SO_3$ at a temperature of 50° C. to 300° C., preferably 150–160° C. The reaction may embody the conditions of the well known Streckerization reaction. The preferred cation M is sodium.

Mass spectral analysis indicates that this mixture contains compounds corresponding to formulas (I), (I-A) and (I-B):

wherein i is an integer from 0 to 10; and R, $R^1$, and M are as defined herein. This mixture is referred to collectively as alkyl diglyceryl ether disulfonates (ADEDS).

Preferably R is straight or branched $C_8$ (such as 2-ethylhexyl), $C_{10}$, $C_{12}$, $C_{13}$, $C_{14}$, or oleyl. Mixtures of compounds of the foregoing formulas are also contemplated. A preferred mixture is that obtained from "Exxal 12", a commercially available mixture of methyl-branched nonanols. The R groups can be synthetic or can be derived from naturally occurring sources such as fatty alcohols, e.g. oleyl alcohol.

Another aspect of the present invention is directed towards methods of preparing an alkylphenol polyethoxy sulfate-sulfonate of formula (III):

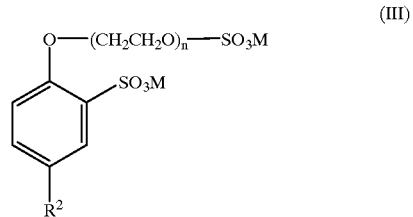

(III)

wherein M is a lithium, sodium, potassium or ammonium cation, $R^2$ is straight or branched alkyl containing 8–12 carbon atoms and n is 6–10.

The process involves the sulfonation of an ethoxylated alkyl phenol of the formula $R^2-Ph-O(CH_2CH_2O)_nH$, wherein $R^2$ and n are as defined above and Ph denotes a phenyl ring and the substituents thereon are in the para-

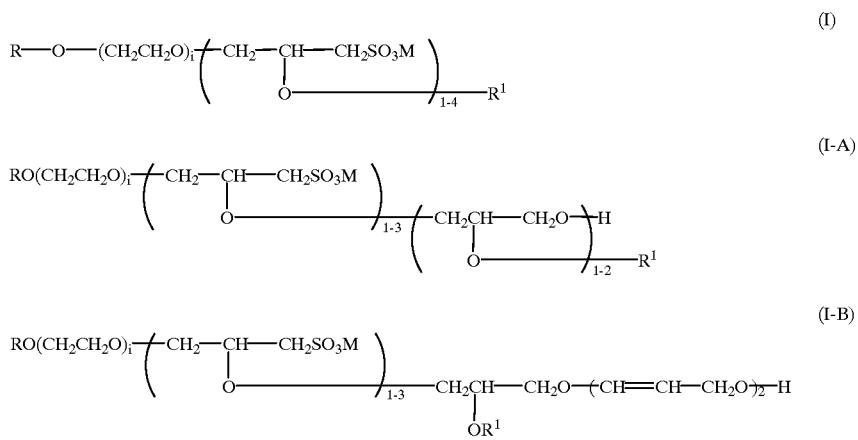

(I)

(I-A)

(I-B)

position, with sulfur trioxide under conditions effective to form an intermediate of formula (IV):

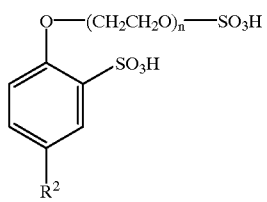

(IV)

Preferably this sulfonation reaction is performed with a 2:1 molar ratio of $SO_3$ to $R^2$—Ph—$O(CH_2CH_2O)_n$H using a continuous air/$SO_3$ thin film sulfonator.

The sulfonated intermediate (IV) is then neutralized with a hydroxide of the formula M—OH and preferably with sodium hydroxide, under conditions wherein said product of formula (III) is formed.

A further aspect of the present invention is directed towards the preparation of an ethoxylated alkylphenol sulfonate of formula (V):

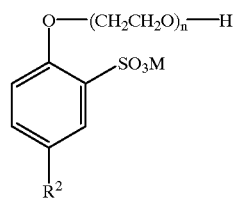

(V)

wherein M is a lithium, sodium, potassium or ammonium cation, $R^2$ is a straight or branched alkyl group containing 8 to 12 carbon atoms, and n is 6 to 10.

The ethoxylated alkylphenol sulfonate of formula (V) is prepared from intermediate (IV) prepared as described above. Preferably, M is a sodium cation.

To prepare the alkylphenol sulfonate (V), the product (IV) is desulfated under conditions such that an ethoxylated sulfonated product is obtained. Preferably, this desulfation is performed by heating an aqueous solution of intermediate (IV) and subsequently neutralizing the solution with an alkali, to obtain an ethoxylated sulfonate of formula (V).

This reaction generates a molar amount of sulfate which separates as a saturated aqueous phase. The saturated aqueous phase can be separated leaving behind a compound of formula (V) containing low levels of alkali sulfate.

In a preferred method, the intermediate (IV) is reacted with 3 moles of concentrated sodium hydroxide, and heated to about 20° C. to 150° C., preferably about 60° C., under conditions wherein said product of formula (V) is formed.

The present invention further contemplates mixtures of alkyl glyceryl ether sulfonate compounds of formulas (I), (I-A) and (I-B):

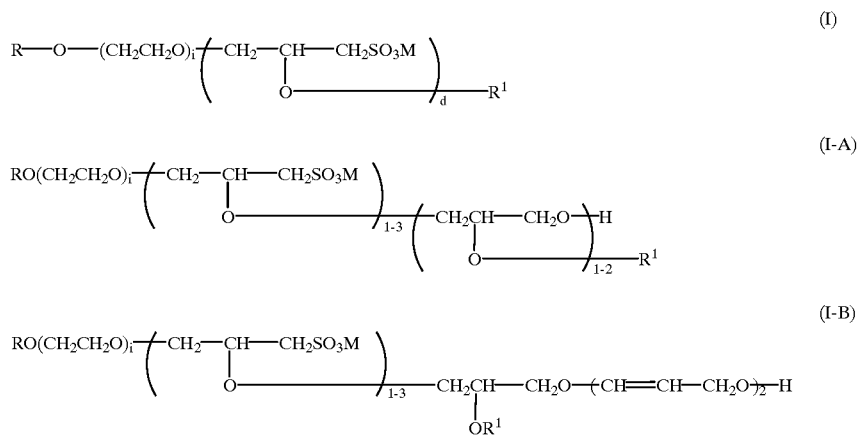

wherein i is an integer from 0 to 10; and R, $R^1$, and M are as defined above.

The present invention further contemplates an alkylphenol polyethoxy sulfate-sulfonate compound of formula (III):

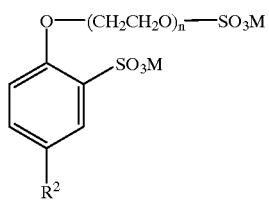

(III)

wherein $R^2$ is straight or branched alkyl of 8 to 12 carbon atoms, and n and M are as defined above.

In a further embodiment of the present invention, the present invention is directed towards an ethoxylated alkylphenol sulfonate compound of formula (V):

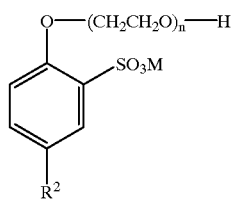

(V)

wherein $R^2$ is straight or branched alkyl containing 8 to 12 carbon atoms, and n and M are as defined above.

EXAMPLE 1

Preparation of Alkylphenol polyethoxy sulfate-sulfonates

Employing the typical procedure for making these compounds, 1.0 mole of a nonylphenol 10-mole ethoxylate was treated with 2.0 moles of $SO_3$ in a laboratory air/$SO_3$ falling-film sulfonating apparatus. The ethoxylate, at about 60° C., was fed to this sulfonator at 8–10 grams per minute, and contacted there with a stream of air/$SO_3$ at about 35° C. The reaction zone was maintained at 70–75° C. A sulfate-sulfonic acid corresponding to formula IV, with $R^2=C_9$ and n=10 (having an acid number of 135–140) was obtained as a dark viscous liquid. This product was then neutralized by addition to a stirred aqueous solution of about 10 wt. % NaOH, which yielded the disodium product of formula III with $R^2=C$, and n=10, as a light tan liquid.

EXAMPLE 2

Preparation of Alkylphenol polyethoxy sodium sulfonates

Employing the typical procedure for making these mixtures of compounds, to a stirred aqueous solution of 50 wt. % sodium hydroxide (3 moles) was added 1.0 mole of the acid of formula IV ($R^2=C_9$) which was formed in Example 1. The heat of neutralization was allowed to raise the temperature of the mixture to 75–80° C. After addition of the acid IV was complete, the mixture was heated to maintain its temperature at 75–80° C. for 2 hours. Heating was then discontinued, and about 1,000 ml of water was added to the mixture which was then stirred for an additional 30 minutes. The mixture was then allowed to cool to 30–40° C. without agitation, and it formed into two distinct aqueous phases. The lower phase (about 650 grams), a saturated aqueous solution of $Na_2SO_4$, was withdrawn and discarded. The upper phase, a tan solution, contained 55–60 wt. % of a compound of formula V with $R^2=C_9$ and n=10.

EXAMPLE 3

Preparation of Alkyl Diglyceryl Ether Disulfonates (ADEDS)

Employing the typical procedure for making these mixtures of compounds, 800 g of lauryl alcohol (containing a minor proportion of $C_{14}$ alcohol) and 8.5 g of boron trifloride etherate were charged to and mixed in a 1-gallon Parr pressure reactor. The reactor was evacuated and pressurized with nitrogen to 60 psi, and vented. The stirred mixture was heated to 50° C., and then 724 g of epichlorohydrin was added slowly to maintain the reaction temperature at 60–70° C. After addition of epichlorohydrin was complete, the mixture was held at 60–70° C. for 60 minutes. The product was a mixture of compounds corresponding to formula II with $R=C_{12}/C_{14}$, i=0, and mono-, di-, tri- and tetra-adducts present wherein the average value of n in the mixture was about 2.

For conversion to the ethoxylate, the mixture was heated to 100° C., and 176 g of ethylene oxide was added over 60 minutes. This formed product of formula II in which $R=C_{12}/C_{14}$, i=0, and —(ALK—O)$_p$H=—(CH$_2$CH$_2$O)$_4$H.

For conversion to the mixture of sulfonates, the product of formula II (1,530 g), 4,600 ml of water and 1,000 g of sodium sulfite were charged to a Parr reactor. The reactor contents were stirred and heated to 160–170° C. (correspondingly the pressure reached 80–100 psi) until the reaction was complete (requiring 10–12 hours) as monitored by assaying for sulfite. The reaction mixture was cooled to 50°C. and sufficient hydrogen peroxide was added to convert residual sulfite to sulfate. This yielded a mixture of sulfonates of formula I wherein $R=C_{12}/C_{14}$, i=0, and $R^1=H$, as a hazy mixture.

Properties and Applications

The alkyl glyceryl ether sulfonate mixtures of formula (I), the alkylphenol polyethoxy sulfate-sulfonates of formula (III), and the ethoxylated alkylphenol sulfonates of formula (V), have a number of useful properties and applications which also comprise aspects of the present invention.

Electrolyte Tolerance/Emulsion Polymerization

One example is in emulsion p-olymerization. This method of polymerization, which is well known in general, is useful in the production of a wide variety of polymers and copolymers, including but not limited to polymerization of: styrene and copolymers of styrene including acrylonitrile-butadiene-styrene, styrene-butadiene and styrene-acrylonitrile; acrylamide; acrylates, methacrylates, and derivatives such as 2-dimethylaminoethyl methacrylate and 2-diethylaminoethyl methacrylate, acrylic acid, methacrylic acid, 2-hydroxyethyl methacrylate and 2-hydroxyethyl acrylate; vinyl chloride, vinyl acetate, vinyl sulfonate, and the like.

Emulsion polymerization is typically carried out starting from an aqueous system containing the monomer(s), one or more surfactants, an initiator system for the polymerization, and optionally other conventional additives. The concentration of the surfactant is generally in the order of 10 to 100 grams per liter, depending chiefly on identity, concentration, and solubility of the monomer(s).

Conventional emulsion polymerization methods often include a step in which an electrolyte such as aluminum sulfate or calcium chloride is added to mediate precipitation of the polymer particle from the aqueous phase. With surfactants conventionally employed heretofore in emulsion polymerization, anionic surfactants are usually found to coprecipitate with the precipitated polymer as the insoluble calcium or aluminum salts. The surfactant which coprecipitates with the polymer is effectively a contaminant and can adversely affect the polymer's properties and its usefulness for certain applications.

The compounds of the present invention (e.g. compounds of formulas (I), (III) and (V)) are useful as surfactants in emulsion polymerization systems. In that application they exhibit the surprising and useful property that they have a significantly reduced tendency to coprecipitate with polymers which are formed via emulsion polymerization.

This reduced tendency to coprecipitate is reflected in the degree of electrolyte tolerance which the compounds of the present invention exhibit. The following example demonstrates electrolyte tolerance of compounds of this invention, and thereby indicates that the compounds of this invention exhibit superior performance in other contexts needing high electrolyte tolerance, such as in emulsion polymerization wherein low coprecipitation of surfactant is an advantage.

EXAMPLE 4

Electrolyte Tolerance

Samples, each 50 ml of 1 wt. % surfactant in water, were prepared. To each stirred sample was added either a 1 wt. % or a 5 wt. % aqueous solution of either aluminum sulfate or calcium chloride. The amount of solution that could be added before the sample became cloudy was recorded, and is set forth in the following Table 1. A higher number for a given electrolyte indicates that more of that electrolyte could be present before the cloudy end point was reached, and thus indicates a higher degree of electrolyte tolerance.

TABLE 1

Electrolyte Tolerance

| Sample | | ml of Electrolyte Added to Cloudy End Point | | | |
|---|---|---|---|---|---|
| | | Aluminum Sulfate | | Calcium Chloride | |
| No. | Surfactant | 1 wt. % | 5 wt. % | 1 wt. % | 5 wt. % |
| — | Sodium dodecyl diphenyl oxide disulfonate[1] | 11 | — | 50 | — |
| 1 | Formula (III), M = Na n = 10 $R^2$ = nonyl | >250 | >250 | >250 | >250 |
| 2 | Formula (V), M = Na n = 10 $R^2$ = nonyl | >250 | >250 | >250 | >250 |
| 3 | Formula (V), M = Na n = 9 $R^2$ = dodecyl | >250 | >250 | >250 | >250 |
| 4 | Formula (III), n = 6, M = Na $R^2$ = nonyl | >250 | >250 | >250 | >250 |
| 5 | Formula (III), M = Na n = 5, $R^2$ = dodecyl | >250 | >250 | >250 | >250 |
| 6 | Formula (III), n = 9, $R^2$ = dodecyl | >250 | >250 | >250 | >250 |
| 7 | Formula (I)[2], i = 0, $R^1$ = H R = $C_{12}/C_{14}$ | >150 | >150 | >150 | >150 |
| 8 | Formula (I)[2], i = 0, $R^1$ = H $(CH_2CH_2O)_4H$ R = $C_{12}C_{14}$ | >150 | >150 | >150 | >150 |
| 9 | Formula (I)[2], i = 0, $R^1$ = $(C_3H_6O)_4H$ R = $C_{12}/C_{14}$ | <30 | <10 | <15 | <4 |

TABLE 1-continued

Electrolyte Tolerance

| Sample | | ml of Electrolyte Added to Cloudy End Point | | | |
|---|---|---|---|---|---|
| | | Aluminum Sulfate | | Calcium Chloride | |
| No. | Surfactant | 1 wt. % | 5 wt. % | 1 wt. % | 5 wt. % |
| 10 | Formula (I)[2], i = 4, $R^1$ = H R = $C_{12}/C_{14}$ | >150 | >150 | >150 | >150 |
| 11 | Formula (I)[2], i = 0, $R^1$ = $(CH_2CH_2O)_8H$ R = $C_{12}/C_{14}$ | >150 | >150 | >150 | >150 |
| 12 | Formula (I)[2], i = 0 $R^1$ = H R = 1,3,5-tri-methyl-nonyl[3] | >150 | >150 | >150 | >150 |
| 13 | Formula (I)[2], i = 0, $R^1$ = H R = 2-ethyl-hexyl | >150 | >150 | >150 | >150 |
| 14 | Formula (I)[2], i = 0, $R^1$ = H R = oleyl | >150 | >150 | >150 | >150 |
| 15 | Formula (I)[2], i = 0, $R^1$ = H R = $C_8/C_{10}$ | >150 | >150 | >150 | >150 |

(1) "Dowfax 2A1", a commercial surfactant
(2) = a mixture of mono-, di-, tri-, tetra- and possibly trace amounts of penta-adducts, wherein the mole average value of d is about 2; and M = Na.
(3) = derived from "Exxal 12"

EXAMPLE 5

As further demonstration of the utility of the products of the present invention in emulsion polymerization, styrene was polymerized in emulsions containing as the surfactant either a mixture of mono-, di-, tri- and tetra-adduct compounds of formula (I), wherein R is 1,3,5-trimethyl nonyl (derived from "Exxal 12"), i=0, M is Na, and the mole average value of n is about 2 and $R^1$ is H (product "DS" in Table 2), or a commercially available sodium $C_{14}/C_{16}$ alpha-olefin sulfonate (compound "AOS" in Table 2).

The polymerizations were run batchwise. Since product DS contained about 5 wt. % of salt, salt was added to the AOS so that each surfactant had the same amount of salt. The batch polymerizations were run at 70° C. for 6 hours with either 1.5 wt. % or 3.0 wt. % surfactant present, and with 0.5 wt. % sodium persulfate as initiator. All weight percentages are expressed herein as % by weight of the initial monomer weight.

The properties of the latexes obtained are set forth in Table 2:

TABLE 2

| Surfactant/concentration | Product yield, % | Particle size, nm |
| --- | --- | --- |
| AOS/1% | 92.7 | 116/48 |
| AOS/3% | 95.9 | 77/22 |
| DS/1% | 79.4 | 98/31 |
| DS/3% | 97.9 | 73/23 |

The data in Table 2 show that the product "DS" is an effective surfactant for emulsion polymerization. At 1% concentration, product "DS" gave substantial coagulum. At 3% concentration, the coagulum was very low and even better than AOS. The stability of the latex emulsion was found to be excellent.

Wetting

The compounds of the present invention are also useful as wetting agents. A particularly valuable application of this property is in the formation of pulp from which paper is made. The pulp comprises water, feedstock, a surfactant component, and optional conventional additives. The feedstock can be recycled material such as paper, paperboard, cardboard, and the like; and can be pulpwood directly from trees, having been suitably processed if desired e.g. by kraft processing, sulfite bleaching, or otherwise; or a mixture of recycled material and pulpwood.

It is desirable to include a surfactant component to increase the rate of wetting, and to increase the extent of wetting, by which the aqueous medium wets the external and interstitial surfaces of the feedstock. Increasing the rate and the extent of wetting are associated with formation of improved pulp, at a faster rate and with a more desirable consistency and quality to the pulp and the paper obtained from it.

In general, wetting is provided by adding 0.1 to 20.0 pounds of surfactant per ton of feedstock, to the pulp. Preferred amounts are 1.0–10 pounds per ton.

The ability to enhance the wetting of the feedstock can be characterized by absorbency rates (rate of water absorption by the feedstock) and by increases in the absorbency rate (as % absorbency rate change, compared to standard). The advantages of using compounds according to the present invention are demonstrated in this way in the following example.

EXAMPLE 6

The determination of wetting was assessed as % absorbency rate change, using standard methods employed in the paper industry.

The compounds tested for % change in the rate of water absorption, and the identities of those compounds, are shown in Table 3.

The ethoxylated alkylphenol sulfonate compounds showed good water absorbency in several feedstocks.

TABLE 3

| | | Absorbency Rates | | |
| --- | --- | --- | --- | --- |
| | Dose (lbs. surfactant/ton of | % Absorbency Rate Change | | |
| Surfactant | feedstock) | 0–5 sec. | 6–12 sec. | 20 sec. |
| Feedstock = Recycled cardboard cartons: | | | | |
| Formula (III), n = 10, $R^2$ = nonyl | 0.5 | +7.7 | +56.0 | +31.3 |
| | 1.0 | +20.5 | +68.0 | +43.4 |
| | 3.0 | +17.9 | +48.0 | +34.5 |
| | 5.0 | +12.8 | +60.0 | +37.5 |
| Formula (V), n = 10, $R^2$ = nonyl | 0.5 | +20.5 | +44.0 | +27.4 |
| | 1.0 | +23.1 | +32.0 | +28.6 |
| | 3.0 | +30.8 | +36.0 | +32.7 |
| | 5.0 | +33.3 | +44.0 | +34.3 |
| Feedstock-Northern softwood (kraft): | | | | |
| Formula (III), n = 10, $R^2$ = nonyl | 0.5 | +18.5 | −9.4 | +5.3 |
| | 1.0 | +9.3 | −5.6 | +5.0 |
| | 3.0 | +13.3 | −13.2 | +3.5 |
| | 5.0 | +22.2 | −9.4 | +10.5 |
| Formula (V), n = 10, $R^2$-nonyl | 0.5 | +35.2 | +1.9 | +14.6 |
| | 1.0 | +31.5 | −7.5 | +9.9 |
| | 3.0 | +40.7 | −5.6 | +14.7 |
| | 5.0 | +57.4 | +3.6 | +30.2 |

EXAMPLE 7

Compounds of the present invention were also tested for their effect on dry tensile strength, and on absorbency (as % change of absorbency rate) of tissue handsheets produced from unbleached recycled fiber (Freeness #303) to which a surfactant of the present invention had been added in the pulp. The results are set forth in Table 4. They show very useful and significant improvement in the properties of the paper product.

TABLE 4

| Surfactant | Dose (lbs. surf./ton of feed-stock) | % Dry Tensile change | % Absorbency Rate Change | | |
| --- | --- | --- | --- | --- | --- |
| | | | 0–5 sec. | 6–12 sec. | 20 sec. |
| Formula (V), n = 10, $R^2$ = nonyl, M = Na | 0.5 | +11.0 | +18.5 | 0 | +11.0 |
| | 1.0 | +5.2 | +21.5 | +12.2 | +16.3 |
| | 3.0 | +3.1 | +26.2 | −5.6 | +12.2 |
| | 5.0 | +6.7 | +29.2 | +11.1 | +24.3 |
| Formula (III), n = 10, $R^2$ = nonyl, M = Na | 0.5 | +14.1 | +32.3 | +19.4 | 29.0 |
| | 1.0 | +7.6 | +30.8 | +27.8 | +34.9 |
| | 3.0 | +20.8 | +10.8 | +2.8 | +9.9 |
| | 5.0 | +20.0 | +3.1 | 0 | +0.7 |
| Formula (I), i = 0 R = $C_{12}/C_{14}$, $R^1$ = $(CH_2OCH_2O)_4H$ M = Na | 1.25 | +41.0 | −13.8 | +11.1 | −10.4 |
| | 2.50 | +48.4 | +18.5 | +19.4 | +16.4 |
| | 7.50 | +34.8 | +10.8 | +11.1 | +7.3 |
| | 12.50 | +46.6 | +16.9 | +12.2 | +16.6 |
| Formula (I), i = 0, $R^1$ = H, R = 1,3,5-trimethyl-nonyl, M = Na | 1.25 | +46.4 | −6.2 | −5.6 | −7.6 |
| | 2.50 | +48.2 | +7.7 | +12.2 | +10.1 |
| | 7.50 | +36.1 | +10.8 | +16.7 | +12.4 |
| | 12.50 | +52.7 | +3.1 | 0 | +0.3 |
| Formula (I), i = 0, | 1.25 | +42.3 | +4.6 | 0 | +6.0 |
| | 2.50 | +45.1 | +12.3 | +12.2 | +11.9 |

TABLE 4-continued

| Surfactant | Dose (lbs. surf./ ton of feed-stock) | % Dry Tensile change | % Absorbency Rate Change | | |
|---|---|---|---|---|---|
| | | | 0–5 sec. | 6–12 sec. | 20 sec. |
| $R^1$ = H, | 7.50 | +33.8 | +24.6 | +22.2 | +23.6 |
| R = $C_{12}/C_{14}$ | 12.50 | +28.6 | +29.2 | +30.6 | +30.2 |
| M = Na | | | | | |

EXAMPLE 8

Compounds of this invention were also tested by standard procedures to determine and correlate the percentage changes in dry and wet tensile strengths, the percentage changes in absorbency rate, and the percentage change in capacity index, in the production of paper tissue and towels from several different feedstocks. The results are set forth in Tables 5–8.

The data demonstrate that the inventive compounds are effective wetting agents. Significantly, they increase the wet/dry tensile ratio when used with a known wet strength resin like "Kymene 557H". The compounds tested had little or no effect on dry tensile (debonding) or density (bulk enhancement). This results in an economic savings because a paper manufacturer would be able to use less wet strength resin.

The data also indicate that absorbance rates, capacities and uptake of the wet strength resin are not significantly changed by alkoxylation or modification of the alkyl moiety. Aromatic sulfonates, (III) and (V), and ADEDS, (I), show excellent performance at dosages of, for example, 1.25–1.5 lbs. per ton.

The compounds of the present invention demonstrate outstanding performance for the production of a range of paper products such as toilet tissue, paper towels, paper napkins, facial tissue, and fine paper. The paper may be creped and pressed, uncreped, and unpressed, including processing wherein the sheet is through dried. The utility of these unique compounds can be further enhanced by formulating them with other surface-active materials including nonionic wetting agents. Preferred materials include alkoxylated $C_8$–$C_{20}$ alcohols, and $C_2$–$C_{20}$ alkylphenols, as well as silicone based surfactants.

In the tests reported in Tables 5–8, each indicated dose size of surfactant was added to the pulp together with 20 pounds per ton of the wet strength resin "Kymene 557H". The tables show however only the dose sizes and the identities of the surfactants used.

TABLE 5

Southern Softwood, Freeness #734

| Surfactant | Dose (lb/ton) | % Dry Tensile Change | % Wet Tensile Change | % Absorb. Rate Change 0–5 Sec. | % Absorb. Rate Change 6–12 Sec. | % Capacity Change Index 20 Sec. |
|---|---|---|---|---|---|---|
| Formula (V), n = 10, $R^2$ = nonyl, M = Na | 1 | −3.0 | +3.6 | +18.8 | +8.7 | +9.8 |
| | 3 | −8.8 | −17.4 | +21.9 | +4.3 | +12.1 |
| | 5 | −1.3 | +7.7 | +31.3 | +17.4 | +20.3 |
| | 10 | −2.2 | +13.3 | +40.6 | +21.7 | +19.5 |

TABLE 5-continued

Southern Softwood, Freeness #734

| Surfactant | Dose (lb/ton) | % Dry Tensile Change | % Wet Tensile Change | % Absorb. Rate Change 0–5 Sec. | % Absorb. Rate Change 6–12 Sec. | % Capacity Change Index 20 Sec. |
|---|---|---|---|---|---|---|
| Formula (I)[1], $R^1$ = $(CH_2CH_2O)_4H$ R = $C_{12}/C_{14}$ i = O, M = Na | 1.25 | +8.6 | +28.6 | +2.2 | 0 | +0.5 |
| | 2.5 | +10.2 | +12.5 | +8.7 | 0 | +5.2 |
| | 7.5 | +17.6 | +22.0 | +8.7 | 0 | +4.1 |
| | 12.5 | −0.7 | +5.0 | +15.2 | −3.6 | +5.9 |
| Formula (I)[1], $R^1$ = H, i = 0, R = 1,3,5-tri-methyl nonyl, M = Na | 1.25 | +16.1 | +22.5 | +8.7 | 0 | +5.9 |
| | 2.5 | +6.5 | +8.5 | +13.0 | 0 | +9.7 |
| | 7.5 | +7.4 | +8.0 | +10.9 | +7.1 | +8.6 |
| | 12.5 | −5.9 | +7.0 | +13.0 | +7.1 | +11.2 |
| Formula (I)[1], $R^1$ = H, i = 0, R = $C_{12}/C_{14}$ M = Na | 1.25 | −1.3 | +13.5 | +10.9 | 0 | +5.8 |
| | 2.5 | −0.9 | +2.5 | +15.2 | +3.6 | +8.0 |
| | 7.5 | +0.9 | +8.5 | +13.0 | +3.6 | +6.2 |
| | 12.5 | −12.6 | +26.5 | +19.6 | +14.3 | +15.0 |
| Formula (I)[1], $R^1$ = H, i = 0, R = 2-ethylhexyl M = Na | 1.25 | +4.1 | −1.5 | +21.8 | 0 | +12.3 |
| | 2.5 | +9.1 | +5.0 | +21.8 | 0 | +11.5 |
| | 7.5 | +6.4 | −8.0 | +21.8 | +3.6 | +13.6 |
| | 12.5 | +14.1 | +20.0 | +26.1 | −3.6 | +12.2 |
| Formula (I)[1], $R^1$ = H, i = 0, R = oleyl M = Na | 1.25 | +16.1 | +19.5 | +6.5 | −3.6 | +2.1 |
| | 2.5 | +9.4 | −8.5 | +6.5 | −3.6 | +1.7 |
| | 7.5 | +4.0 | +11.5 | +8.7 | −3.6 | +4.6 |
| | 12.5 | +3.4 | −1.5 | +19.6 | +7.1 | +14.5 |
| Formula (I)[1], i = 0, $R^1$ = $(CH_2CH_2O)_8H$ R = $C_{12}/C_{14}$ M = Na | 1.25 | +1.6 | +37.4 | +13.0 | +7.1 | +8.2 |
| | 2.5 | +2.2 | +16.7 | +8.7 | +3.6 | +6.4 |
| | 7.5 | +5.9 | +21.8 | +21.8 | 0 | +12.5 |
| | 12.5 | −13.1 | +1.5 | +28.3 | +10.7 | +17.1 |
| Formula (I)[1], i = 4, $R^1$ = H R = $C_{12}/C_{14}$ M = Na | 1.25 | −2.2 | +21.2 | +21.8 | 0 | +14.1 |
| | 2.5 | −7.7 | +16.7 | +23.9 | 0 | +12.8 |
| | 7.5 | −9.9 | +25.1 | +30.4 | 0 | +16.1 |
| | 12.5 | −13.1 | +3.0 | +23.9 | 0 | +12.4 |

(1): A mixture of compounds in which n was each of 1–5 and its mole average value was about 2.

TABLE 6

TISSUE - HANDSHEET DATA
Northern Softwood Kraft, Freeness #681

| Surfactant | Dose (lb/ton) | % Dry Tensile Change | % Wet Tensile Change | % Rate of Absorb. Chg. 0–5 sec. | % Rate of Absorb. Chg. 6–12 sec. | % Rate of Absorb. Chg. 20 sec. |
|---|---|---|---|---|---|---|
| Formula (V), n = 10, $R^2$ = nonyl M = Na | 1.0 | +4.1 | +44.2 | +14.3 | +7.8 | +11.2 |
| | 3.0 | −3.2 | +7.2 | +9.5 | −7.8 | −5.5 |
| | 5.0 | 0 | +25.7 | +9.5 | 0 | +4.9 |
| | 10.0 | −13.0 | −9.4 | +9.5 | +7.8 | +4.4 |
| Formula (I)[1], $R^1$ = $(CH_2CH_2O)_4H$ R = $C_{12}/C_{14}$ i = 0 M = Na | 1.25 | +3.4 | +21.0 | +4.5 | −9.9 | +0.8 |
| | 2.50 | −2.7 | +4.9 | −9.1 | −26.8 | −13.6 |
| | 7.50 | −4.3 | +12.8 | −11.8 | −25.4 | −13.8 |
| | 12.50 | −13.5 | +18.7 | +9.1 | −5.6 | +5.7 |
| Formula (I)[1], $R^1$ = H, i = 0, R = $C_{12}/C_{14}$ | 1.25 | +5.4 | +27.4 | +18.2 | −8.5 | +7.9 |
| | 2.50 | +8.8 | +20.2 | +13.6 | −9.9 | +4.4 |
| | 7.50 | +6.7 | +15.8 | +9.1 | −4.2 | +5.7 |

TABLE 6-continued

TISSUE - HANDSHEET DATA
Northern Softwood Kraft, Freeness #681

| Surfactant | Dose (lb/ton) | % Dry Tensile Change | % Wet Tensile Change | % Rate of Absorb. Chg. 0–5 sec. | % Rate of Absorb. Chg. 6–12 sec. | % Rate of Absorb. Chg. 20 sec. |
|---|---|---|---|---|---|---|
| M = Na | 12.50 | +8.1 | +31.7 | +22.7 | +5.6 | +16.4 |
| Formula (I)[1], | 1.25 | +5.5 | +20.3 | +14.3 | 0 | +8.0 |
| i = 0, | 2.50 | +5.7 | +8.1 | +4.8 | 0 | +2.4 |
| $R^1$ = | 7.50 | +0.9 | +8.9 | +9.5 | −5.9 | +6.7 |
| $(CH_2CH_2O)_8H$ | 12.50 | −1.2 | +25.8 | +28.6 | 0 | +17.5 |
| R = $C_{12}/C_{14}$ | | | | | | |
| M = Na | | | | | | |
| Formula (I)[1], | 1.25 | +2.3 | +20.3 | +19.0 | 1.5 | +13.7 |
| i = 0, | 2.50 | +4.1 | +13.7 | +9.5 | −5.9 | +6.4 |
| $R^1 = (C_3H_6O)_4H$ | 7.50 | +1.1 | +20.3 | +14.3 | −5.9 | +9.6 |
| R = $C_{12}/C_{14}$ | 12.50 | +2.5 | +11.4 | +14.3 | +7.4 | +11.6 |
| M = Na | | | | | | |
| Formula (I)[1], | 1.25 | +8.2 | +34.3 | +4.8 | −2.9 | +3.0 |
| $R^1$ = H, i = 0, | 2.50 | −1.6 | +5.9 | +4.8 | −2.9 | +2.0 |
| R = 2-ethylhexyl | 7.50 | −1.1 | +36.9 | +9.5 | 0 | +5.2 |
| M = Na | 12.50 | −2.0 | +14.8 | +19.0 | +7.4 | +12.8 |
| Formula (I)[1], | 1.25 | +1.8 | +49.4 | +14.3 | +8.8 | +12.9 |
| $R^1$ = H, i = 0, | 2.50 | −3.0 | +12.5 | +14.3 | +8.8 | +12.8 |
| R = oleyl | 7.50 | +0.6 | +23.2 | +19.1 | +13.2 | +16.1 |
| M = Na | 12.50 | −7.2 | +12.5 | +19.0 | +11.8 | +16.3 |

(1): A mixture of compounds in which n was each of 1–5 and its mole average value was about 2.

TABLE 7

Recycled Cartons, Freeness #440

| Surfactant | Dose (lb/ton) | % Dry Tensile Change | % Wet Tensile Change | % Absorb. Rate Change 0–5 sec. | % Absorb. Rate Change 6–12 sec. | % Absorb. Rate Change 20 sec. |
|---|---|---|---|---|---|---|
| Formula (V), | 1 | +11.3 | +24.6 | +19.5 | +16.2 | +19.0 |
| n = 10, | 3.0 | +8.8 | +0.6 | +18.2 | +13.5 | +15.8 |
| $R^2$ = nonyl | 5.0 | +7.0 | +15.0 | +22.1 | +13.5 | +20.7 |
| M = Na | 10.0 | +6.1 | +1.8 | +23.4 | +10.8 | +20.7 |
| Formula | 1.25 | +2.7 | +21.0 | +5.2 | +8.1 | +7.2 |
| (I)[1], i = 0, | 2.50 | +5.5 | +0.3 | +2.6 | +8.1 | +6.5 |
| $R^1$ = | 7.50 | +4.3 | +15.3 | +2.6 | +8.1 | +4.8 |
| $(CH_2CH_2O)_8H$ | 12.50 | +5.4 | +6.0 | +9.1 | +13.5 | +11.2 |
| R = $C_{12}/C_{14}$ | | | | | | |
| M = Na | | | | | | |
| Formula | 1.25 | +7.8 | +13.5 | 0 | +13.5 | +5.3 |
| (I)[1], i = 4, | 2.50 | +4.8 | 0 | −2.6 | +2.7 | +1.0 |
| $R^1$ = H, | 7.50 | +9.6 | +15.6 | +11.7 | +10.8 | +12.7 |
| R = $C_{12}/C_{14}$ | 12.50 | +2.6 | +3.0 | +9.1 | +13.5 | +10.2 |
| M = Na | | | | | | |
| Formula | 1.25 | +8.4 | +2.4 | −1.3 | −2.7 | −2.0 |
| (I)[1], $R^1$ = H, | 2.50 | +4.3 | 0 | +13.0 | +2.7 | +11.7 |
| i = 0, R = 2-ethylhexyl | 7.50 | +10.3 | +21.6 | +15.6 | +13.5 | +14.0 |
| M = Na | 12.50 | +2.7 | +1.5 | +16.9 | +13.5 | +15.0 |
| Formula | 1.25 | +2.7 | +21.6 | +15.6 | +5.4 | +13.5 |
| (I)[1], $R_1$ = H, | 2.50 | +2.0 | −3.0 | +10.4 | +2.7 | +7.4 |
| i = 0, | 7.50 | −6.7 | +19.8 | +7.8 | 0 | +4.8 |
| R = oleyl | 12.50 | −8.4 | +9.3 | +18.2 | +13.5 | +17.8 |
| M = Na | | | | | | |
| Formula | 1.25 | +8.6 | +24.9 | +5.5 | +10.3 | +8.1 |
| (I)[1], $R^1$ = | 2.50 | +4.2 | +8.4 | −5.5 | −7.7 | −5.1 |
| $(CH_2CH_2O)_4H$ | 7.50 | +7.3 | +19.7 | −4.1 | −12.8 | −5.2 |

TABLE 7-continued

Recycled Cartons, Freeness #440

| Surfactant | Dose (lb/ton) | % Dry Tensile Change | % Wet Tensile Change | % Absorb. Rate Change 0–5 sec. | % Absorb. Rate Change 6–12 sec. | % Absorb. Rate Change 20 sec. |
|---|---|---|---|---|---|---|
| R = $C_{12}/C_{14}$ | 12.50 | +1.0 | +15.4 | +13.7 | +5.2 | +14.0 |
| i = 0 | | | | | | |
| M = Na | | | | | | |
| Formula | 1.25 | +14.4 | +19.1 | +1.4 | −2.6 | −0.2 |
| (I)[1], i = 0 | 2.50 | +6.0 | +7.0 | −1.4 | −5.1 | −0.6 |
| $R^1$ = H | 7.50 | +7.9 | +27.8 | +4.1 | 0 | +2.8 |
| R = 1,3,5-trimethyl-nonyl | 12.50 | +13.0 | +10.7 | +5.5 | +10.3 | +7.0 |
| M = Na | | | | | | |
| Formula | 1.25 | 9.5 | +27.0 | +16.4 | +10.3 | +17.4 |
| (I)[1], $R^1$ = H, | 2.50 | +11.8 | +9.0 | +8.2 | +10.3 | +10.0 |
| i = 0, | 7.50 | +10.2 | +22.6 | +1.4 | +5.2 | +3.9 |
| R = $C_{12}/C_{14}$ | 12.50 | +8.4 | +12.8 | +5.5 | +10.3 | +6.6 |
| M = Na | | | | | | |

(1): A mixture of compounds in which n was each of 1–5 and its mole average value was about 2.

TABLE 8

TOWEL - HANDSHEET DATA

| Surfactant | Dose (lb/ton) | % Dry Tensile Change | % Wet Tensile Change | % Absorb. Rate Change 0–5 sec. | % Absorb. Rate Change 6–12 sec. | % Capacity Index Change 20 sec. |
|---|---|---|---|---|---|---|
| Feedstock = Screened Recycled Fiber (Freeness #437) | | | | | | |
| Formula (V), | 1 | +6.4 | +48.8 | −5.7 | −8.7 | −6.0 |
| n = 10, | 3 | +4.6 | −3.3 | −34.3 | −43.5 | −40.7 |
| $R^2$ = nonyl | 5 | +8.2 | +12.5 | −31.4 | −39.1 | −34.7 |
| M = Na | 10 | +2.2 | −5.0 | −14.3 | −17.4 | −15.1 |
| Feedstock = CTMP (Freeness #582) | | | | | | |
| Formula (V), | 1 | +0.5 | +31.1 | +10.3 | +14.3 | +6.1 |
| n = 10, | 3 | −5.0 | −2.7 | +28.2 | +35.8 | +15.9 |
| $R^2$ = nonyl | 5 | +13.5 | +14.2 | +35.9 | +32.1 | +12.7 |
| M = Na | 10 | −14.1 | −12.8 | +33.3 | +28.6 | +12.7 |
| Feedstock = Blend NOC (Freeness #585) | | | | | | |
| Formula (V), | 1 | +11.6 | +10.5 | +10.0 | +16.7 | +11.3 |
| n = 10, | 3 | +9.3 | −15.7 | −5.0 | 0 | −4.0 |
| $R^2$ = nonyl | 5 | +14.9 | +15.7 | +5.0 | +16.7 | +5.0 |
| M = Na | 10 | +2.2 | −16.9 | +10.0 | +16.7 | +12.6 |
| Feedstock = Sulfite (Freeness #707) | | | | | | |
| Formula (V), | 1 | +5.6 | +11.5 | 0 | −6.1 | −4.9 |
| n = 10, | 3 | −14.2 | −19.1 | +27.1 | +15.2 | +42.9 |
| $R^2$ = nonyl | 5 | −9.5 | −13.7 | −12.5 | −3.0 | −9.0 |
| M = Na | 10 | −9.4 | +1.6 | +66.7 | +93.4 | +82.6 |
| Feedstock = Softwood/CTMP (50:50) (Freeness #654) | | | | | | |
| Formula (V), | 1 | +0.8 | −7.9 | −14.6 | −6.7 | −13.0 |
| n = 10, | 3 | +4.0 | +9.0 | −9.8 | −13.3 | −7.9 |
| $R^2$ = nonyl | 5 | −3.3 | +17.4 | 0 | −20.0 | −6.4 |
| | 10 | −1.2 | −11.2 | +22.0 | −20.0 | +3.7 |

Dye Leveling

During dyeing of a fiber it is important that the dye is evenly distributed throughout the fiber. This is known as dye-leveling. The alkyl diglyceryl ether disulfonate (I), alkylphenol polyethoxy sulfate-sulfonate (III), and ethoxylated alkylphenol sulfonate (V) compounds of the present invention are useful in that when a fiber is being dyed, such as a nylon fiber, they assist attaining uniform distribution of dye throughout the fiber being dyed. This property is useful for instance in the carpet industry. In general, one can use effective amounts ranging generally form 0.5% to 5% by weight of surfactant based on the weight of dye.

EXAMPLE 9

The compounds of the present invention were tested as dye-levelers and compared to "Dowfax 2A1", a commercially important dye-leveling additive.

Preparation of Dye Stock

A trichromic dye stock solution was prepared by mixing 21.0 grams of 0.5% Ciba Tectilon orange 3G200, 10.5 grams of 0.5% Ciba Tectilon blue 4RS KWL 200, 10.5 grams of 0.5% Ciba Tectilon red 2KWL 200N with 2.0 grams of ammonium sulfate. The mixture was diluted to 4000 grams with tap water and mixed well.

Nylon Dye Leveling 400 gram aliquots of the dye stock solution were poured into stainless steel cylinders, and the surfactant to be tested was added, 0.1 grams to 1.0 gram of 10% active. "Dowfax 2A1" was used for comparison. The material was mixed and adjusted to pH 5.8–6.0 with 10% acetic acid. A 10 gram swatch of Nylon 6 Barre (tiger) cloth, from Monsanto Co., was added along with 3–4 stainless steel balls. The cylinder was sealed and placed in an Atlas Laundrometer at 20° C. The cylinders were heated to BOOC, at an average rate of 1° C./minute, for 60 minutes. The cylinders were cooled to 30° C., the swatch removed, rinsed with tap water and allowed to air dry overnight. The dried swatches were analyzed on the Hunter Lab D25M/L calorimeter and the L values (whiteness and brightness) recorded. The data obtained on the two ends, lengthwise, of each swatch is expressed as % leveling.

The results are shown in Table 9. The compounds of the present invention performed as well as or better than "Dowfax 2A1".

TABLE 9

| | Dye Leveling | |
|---|---|---|
| Suractant | Concentration (wt. %) | % Dye Leveling |
| "Dowfax 2A1" | 0.015 | 83.8 |
| | 0.0075 | 97.7 |
| Formula (I), i = 0, $R^1$ = H, R = 1,3,5-trimethyl-nonyl | 0.015 | 96.8 |
| | 0.0075 | 94.6 |
| Formula (I), i = 0, $R^1$ = $(C_3H_6O)_4H$ R = $C_{12}/C_{14}$ | 0.0075 | 95.8 |
| Formula (I), i = 0, $R^1$ = $(CH_2CH_2O)_8H$ R = $C_{12}$–$C_{14}$ | 0.0075 | 99.4 |
| Formula (V), n = 10 $R^2$ = nonyl | 0.015 | 98.6 |
| Formula (III), n = 10 $R^2$ = nonyl | 0.015 | 97.0 |

Froth Flotation

The compounds of the present invention are also useful as frothers in the froth flotation beneficiation of ores. A particular example is the froth flotation of phosphate ore to separate impurities present in the ore as it naturally occurs. In general, flotation can be carried out by slurrying water and the finely divided ore in a cell with the surfactant of the present invention in amounts of about 0.02 to 2.0 pounds of surfactant per ton of ore (preferably, 0.025 to 1.0 pounds of surfactant per ton of ore). Other additives can also be present, such as tall oil fatty acids (TOFA) as auxiliary frother; other possible additives can include collectors and depressants, as needed in the amounts useful to achieve those functions.

Air is then circulated into the cell at its bottom and upwards through the slurry, at a flow rate effective to form a froth in the slurry. The froth containing the impurities is skimmed off continuously, or otherwise removed, all in accordance with known techniques.

EXAMPLE 10

The effectiveness of the compounds of the present invention in froth flotation for the beneficiation of ores was measured using known standard methods. The results for phosphate ore flotation using compounds of this invention in combination with tall oil fatty acids are shown in Table 10. The beneficiation observed for phosphate rock even at 0.04 lbs/ton using the lauryl alcohol based ADEDS mixtures is noteworthy.

TABLE 10

| Surfactant | Amt. (lb. /ton of ore) | TOFA[1] (lb./ton) | % Phosphate Recovery |
|---|---|---|---|
| (None) | — | 1.0 | 11.0 |
| (None) | — | 2.0 | 64.0 |
| Formula $(I)^2$, i = 0, $R^1$ = H, M = Na R = $C_{12}/C_{14}$ | 0.75 | 1.0 | 86.0 |
| Formula $(I)^2$, i = 0, $R^1$ = H, M = Na R = $C_{12}/C_{14}$ | 0.04 | 1.0 | 48.0 |
| Formula $(I)^2$, i = 0, M = Na $R^1$ = $(CH_2CH_2O)_8H$ R = $C_{12}/C_{14}$ | 0.75 | 1.0 | 89.0 |

(1) = TOFA is tall oil fatty acids.
(2) = A mixture of compounds in which n is each 1–5 and its mole average value is about 2.

Hard Surface Cleaners, Stain Removers, and Laundry Detergents

The compounds of the present invention are also useful in cleaning substrates ranging from fabrics and carpeting, to hard surfaces such as floors, porcelain fixtures, countertops, and the like. They can be formulated into cleaning products containing 0.1 to 20 wt. % or more, of one or more compounds of the present invention. Several compounds of the present invention were tested as laundry detergents using test methods well known in the industry. The results are shown in Example 11 and Table 11.

The low molecular weight and branched compounds of formula (I) were found to be good compatibility agents and good lime-soap dispersants even at low pH. The ADEDS were also found to be efficient spot removers for laundry applications.

EXAMPLE 11

Swatches of fabric which were soiled or stained were prepared and washed using various compounds of the present invention as the soil removal/stain removal surfactant. The degree of effectiveness, as % removal, was then determined. The washing was carried out in 100 ppm hardness water at 70° F., in 1-liter of wash water containing 1 gram of surfactant (=1 gpl). The wash cycle was 10 minutes, the rinse cycle was 5 minutes, agitation was at 100 rpm, and the rinsed swatches were air dried overnight. The results were:

TABLE 11

| | | % Soil/Stain Removal | | |
|---|---|---|---|---|
| | | Surfactants: | | |
| Fabric | Soil/Stain | A | B | C |
| Cotton | Clay | 71.6 | 72.7 | 79.9 |
| Cotton | Olive oil | 79.8 | 84.6 | 93.4 |
| Cotton/ polyester | Coffee | 79.9 | 85.7 | 87.1 |
| Cotton/ polyester | Grape juice | 81.6 | 92.0 | 93.6 |

Surfactant
A: Formula (I), i = 0, $R^1$ = H, R = 1,3,5-trimethyl-nonyl, M = Na
B: Formula (I), i = 0 $R^1$ = $(CH_2CH_2O)_4H$, R = $C_{12}/C_{14}$, M = Na
C: Dodecylbenzene sulfonic acid, sodium salt Paper Deinking The compositions of the present invention are also useful in deinking of waste paper. While paper deinking is known, it is summarized here.

In general, effective deinking is provided by intimately contacting the waste paper with any of the compositions of the present invention, preferably in an aqueous or other liquid medium to provide desired fluidity and penetration of the surfactant components to the paper/ink interface. Preferably, the waste paper is first shredded or otherwise converted to small pieces so as to improve the contact of the paper and ink with the liquid medium bearing the surfactants. Of course, appropriate agitation can be provided to enhance the desired contact between the surfactant components and the paper/ink interface.

It is preferred to utilize the compositions of the present invention in connection with the froth flotation of ink from the waste paper. The general conditions of froth flotation deinking techniques are known in this field. The waste paper is pulped in an aqueous bath, which has preferably been rendered alkaline by appropriate adjustment of the pH via the addition of a base such as sodium hydroxide. Preferably, the pH is about 9 to 11. The desired composition or compounds of the present invention are added at amounts calculated to provide the desired ratio between amounts of the respective compounds. The overall amount of product to use is selected with respect to the quantity of the paper in the cell and with respect to the general amount of ink product on the paper. Generally, the total amount of product comprises about 0.05–0.1 wt. % to about 5.0 wt. % and preferably up to about 1.0 wt. % based on the amount of waste paper present. Lesser amounts risk reducing the efficiency of the deinking, whereas higher amounts may assist in the deinking of waste paper but not necessarily enhance the efficiency of the deinking in proportion to the additional amounts of product used. The flow of gas, typically air, through the flotation cell agitates the liquid medium and the waste paper, provides enhanced contact with the product, and propels ink particles removed from the waste paper to the top surface where a froth rich in removed ink is established. The froth can be removed or continuously or intermittently. After a period of time appropriate for the volume of the cell and the quantity of waste paper and its ink content, the pulp of deinked waste paper is removed from the cell for further processing toward the recovery and reuse in regenerated paper products.

The present invention has been found to provide improved effectiveness and efficiency in the deinking of waste paper, particularly waste paper comprising mixtures of different types of paper.

EXAMPLE 12

To demonstrate the effectiveness in paper deinking of compositions containing compounds of formula (I), the following comparative tests were carried out.

EXPERIMENTAL PROCEDURE

Repulping

A furnish of mixed office waste consisting of 70% laser-printed paper and 30% ledger paper was repulped in a Modern Laboratory Slush-Maker at 2900 rpm, and 6% consistency. Initially water (28.4 liters) was added, then steam was injected to increase the temperature to 120° F. Four pound (O.D.) batches were added over 5 minutes to maintain stock circulation in the Slush-Maker. The pH was adjusted to 10 with 5% NaOH. The repulping was performed at the following conditions:

| Consistency | 6% |
|---|---|
| Temperature | 120° F. |
| pH | 10 |
| Repulping time | 30 minutes |

After repulping the stock from the Slush-Maker was diluted to approximately 0.75–0.08% consistency to make a "master batch". The temperature of the master batch was adjusted to 100° F. before it was fed to the flotation cell.

Flotation

Flotation was performed in a laboratory-scale flotation cell. The furnish was added manually at approximately 0.8% consistency to the flotation cell which has a 7.7 gallon capacity. The furnish was recirculated in the flotation cell at 15 gal/minute for mixing. The surfactants as identified in Table 12 were allowed to mix five minutes prior to starting the compressed air flow to cell. The air flow was fed at 8 $ft^3$/minute. All the surfactants were diluted to 68.1 gms/liter and added at 0.3, 0.6 and 0.9%, based on dry solids. Inky foam formed on the surface is rejected out the center of the cell while accepts remain in the cell. The flotation cell was operated for ten minutes while collecting rejects. Six flotation runs were performed at different surfactant addition levels with one master batch. Samples of feed and accepts were collected for brightness pads. Rejects were collected and weighted for yield calculation.

Brightness Pads

After repulping and flotation, portions of the furnish were taken to make brightness pads (TAPPI Standard T-218). Five air dried brightness pads were made for brightness and dirt count. Brightness was measured (two readings on each side of five sheets) on the pad surface using S4-M a brightmeter.

Yield

The flotation yield was calculated using the equation below.

Capacity of flotation cell = 7.69 gallons
Mass of flotation cell = 29121 grams
$C_F$ = Consistency of Feed
$C_R$ = Consistency of Reject
$W_R$ = Weight of reject $$Yeild = \frac{100 \times ((29121 \times C_F) - (W_R \times C_R))}{(29121 \times C_F)}$$

Image analysis

Particle count measurements were performed on a Spec "Scan" image analyzer. It uses a HP Scan Jet scanner to digitize the image of the paper samples at resolutions up to 800 dots per inch, that is, it can detect dirt and/or ink specks as small as 0.032 mm in diameter or about 0.001 mm² and counts and categorizes the specks size. Scanning was performed only for the MOW furnish. Ten four inch round circles were scanned for each samples. The total area scanned for each sample was 0.042 m². The scanner settings are the following:

Resolution: 600 dots/inch
Threshold: 80 manual

The results obtained are set forth in Table 12:

TABLE 12

Furnish: Old Newsprint (ONP)/Old Magazine (OMG)
(70% ONP, 30% OMG)

| Surfactant | % Addition | % Brightness Increase | % Fiber Yield |
|---|---|---|---|
| 1 | 0.3 | 14.55 | 95.87 |
|   | 0.6 | 13.90 | 91.33 |
|   | 0.9 | 13.82 | 89.90 |
| 2 | 0.3 | 12.21 | 94.05 |
|   | 0.6 | 10.68 | 90.86 |
|   | 0.9 | 10.59 | 87.49 |
| 3 | 0.3 | 7.24 | 98.48 |
|   | 0.6 | 6.64 | 98.38 |
|   | 0.9 | 5.51 | 98.52 |
| 4 | 0.3 | 9.17 | 97.37 |
|   | 0.6 | 8.72 | 95.67 |
|   | 0.9 | 8.61 | 93.82 |

Legend:
1: "Lionsurf 727", a commercial standard.
2: "DI-600", a commercial standard.
3: Mixture of compounds of Formula I, $R^1$ = H,
 i = o, R = trimethyl nonyl
4: #3 (60%) + "Witconol NS500 LQ". (40%)
 "Witconol NS 500 LQ" is a commercial alkoxylated alcohol Furnish: Mixed Office Waste (MOW)
(70% laser, 30% ledger)

| Surfactant | % Addition | % Brightness Increase | % Fiber Yield | % Visible Dirt Decreases (>0.005 mm²) | % TAPPI Dirt count decreases (>0.04 mm²) |
|---|---|---|---|---|---|
| 1 | 0.3 | 17.49 | 95.29 | 98.64 | 94.03 |
|   | 0.6 | 15.74 | 92.88 | 94.94 | 87.08 |
|   | 0.9 | 14.60 | 91.96 | 91.89 | 79.24 |
| 2 | 0.3 | 18.53 | 95.84 | 99.13 | 97.18 |
|   | 0.6 | 18.7S | 94.54 | 97.22 | 91.81 |
|   | 0.9 | 17.03 | 94.44 | 94.82 | 89.70 |
| 3 | 0.3 | 28.54 | 98.11 | 99.49 | 98.79 |
|   | 0.6 | 2S.34 | 97.54 | 99.51 | 98.98 |
|   | 0.9 | 26.02 | 96.41 | 99.43 | 99.39 |
| 4 | 0.3 | 25.24 | 98.00 | 99.72 | 99.04 |
|   | 0.6 | 25.40 | 95.58 | 99.90 | 99.78 |
|   | 0.9 | 24.41 | 94.88 | 99.70 | 98.95 |

Legend:
1: "Lionsurf 727", a commercial standard.
2: "DI-600", a commercial standard.
3: Mixture of compounds of Formula I, $R^1$ = H,
 i = o, R = trimethyl nonyl.
4: #3 (60%) + "Witconol NS 500LQ" (40%)
 ("Witconol NS500 LQ" is an alkoxylated alcohol.

| Surfactant Reference | Addition % | Feed % | Accepts % | Delta Bright % | Increase % | Yield % |
|---|---|---|---|---|---|---|
| 1 | 0.3 | 35.21 | 31.86 | 3.35 | 9.51 | 90.98 |
|   | 0.6 | 35.21 | 31.94 | 3.27 | 9.29 | 88.89 |
|   | 0.9 | 35.21 | 32.44 | 2.77 | 7.87 | 88.95 |
| 2 | 0.3 | 36.02 | 31.86 | 4.16 | 11.55 | 90.77 |
|   | 0.6 | 36.02 | 31.53 | 4.49 | 12.47 | 91.56 |
|   | 0.9 | 36.02 | 33.21 | 2.81 | 7.80 | 91.56 |
| 3 | 0.3 | 34.52 | 32.43 | 2.09 | 6.05 | 98.95 |
|   | 0.6 | 34.52 | 32.23 | 2.29 | 6.63 | 98.53 |
|   | 0.9 | 34.52 | 33.23 | 1.29 | 3.74 | 94.27 |
| 4 | 0.3 | 33.4 | 30.14 | 3.26 | 9.76 | 92.55 |
|   | 0.6 | 33.4 | 28.86 | 4.54 | 13.59 | 91.61 |
|   | 0.9 | 33.4 | 28.52 | 3.88 | 11.62 | 91.54 |

Legend:
1: "Lionsurf 727", a commercial standard.
2: "DI-600", a commercial standard.
3: Mixture of compounds of Formula I, $R^1$ = H, i = o, R = trimethyl nonyl.
4: #3 (60%) + "Witconol NS 500LQ" (40%) ("Witconol NS500 LQ" is an alkoxylated alcohol.

What is claimed is:

1. A method of preparing an alkyl glyceryl ether sulfonate composition which comprises a mixture of sulfonate compounds of formulas (I), (I-A) and (I-B)

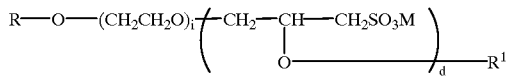
(I)

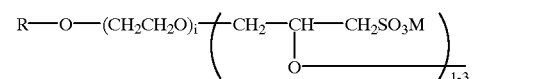
(I-A)

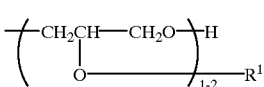

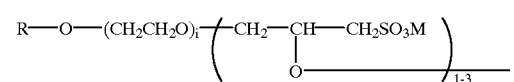
(I-B)

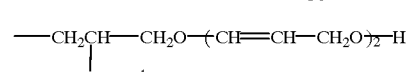

wherein i is an integer from 0 to 10;
M is selected from the group consisting of lithium, sodium, potassium, and ammonium cations and mixtures thereof;
$R^1$ is $(ALK—O)_p H$ or H, wherein p is an integer from 0 to 10, each ALK is independently ethyl or propyl; and
R is straight or branched alkyl or alkenyl containing 8 to 18 carbon atoms and 0 to 3 carbon-carbon double bonds, wherein the mixture contains compounds of formula (I) wherein d is 1, 2, 3. and 4 and optionally 5, wherein the mole average value of d in the mixture is 1.8 to 2.2, the method comprising:

(a) forming a mixture of glyceryl halides of formulas (II), (II-A), and (II-B)

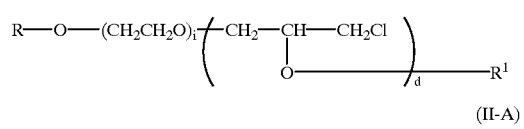
(II)

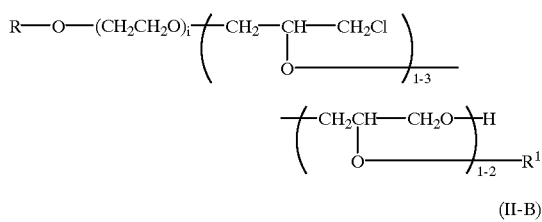
(II-A)

(II-B)

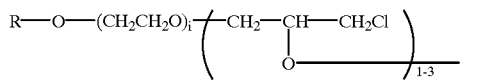

-continued

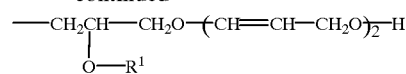

by reacting epichorohydrin with an alcohol or alcohol ethoxylate of the formula R—O—(CH$_2$CH$_2$O)$_i$—H to form the mixture of glyceryl halides of formulas (II), (II-A), and (II-B), and optionally alkoxylating the pendant hydroxyl group on the compounds of formula (II); and then (b) a replacing the chloro substituents on the compounds of formulas (II), (II-A), and (II-B) with —SO$_3$M, thereby forming the mixture of sulfonate compounds.

2. A method according to claim 1 wherein i is zero.

3. A method according to claim 1 wherein each ALK group is ethyl.

4. A method according to claim 1 wherein each ALK group is propyl.

5. A method according to claim 1 wherein in step (a) the pendant hydroxyl group on said compounds of formula (II) is alkoxylated such that R$^1$ is (ALK—O)$_p$H.

6. A method according to claim 1 wherein M is sodium.

7. A composition of compounds of formula (I) produced by the process of claim 1.

* * * * *

UNITED STATES PATENT AND TRADEMARK OFFICE
Certificate

Patent No. 5,919,975

Patented: July 6, 1999

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: John Gray, Crown Point, IN; Jeffrey J. Fulton, Janesville, WI; and Khalid Rasheed, Powell, OH.

Signed and Sealed this Sixteeth Day of November, 1999.

ROBERT GERSTL
*Primary Examiner*
Art Unit 1613